(12) United States Patent
Gatzweiler et al.

(10) Patent No.: US 8,492,313 B2
(45) Date of Patent: Jul. 23, 2013

(54) SYNERGISTIC HERBICIDAL COMBINATIONS COMPRISING TEMBOTRIONE

(75) Inventors: Elmar Gatzweiler, Büdingen (DE); Klaus Trabold, Heidelberg (DE); Erwin Hacker, Hochheim (DE); Frank Ziemer, Kriftel (DE); Alfred Angermann, Kriftel (DE)

(73) Assignee: Bayer Cropscience AG, Monheim (DE)

( * ) Notice: Subject to any disclaimer, the term of this patent is extended or adjusted under 35 U.S.C. 154(b) by 297 days.

(21) Appl. No.: 12/786,850

(22) Filed: May 25, 2010

(65) Prior Publication Data

US 2010/0311588 A1 Dec. 9, 2010

(30) Foreign Application Priority Data

May 27, 2009 (EP) .................................... 09007061

(51) Int. Cl.
*A01N 41/02* (2006.01)
(52) U.S. Cl.
USPC ........... 504/350; 504/118; 504/130; 504/133; 504/136; 504/137; 504/138
(58) Field of Classification Search
USPC ................. 504/118, 130, 133, 137, 138, 350
See application file for complete search history.

(56) References Cited

U.S. PATENT DOCUMENTS

| 6,919,299 | B2 * | 7/2005 | Hacker et al. | 504/141 |
| 2008/0004180 | A1 * | 1/2008 | Dollinger et al. | 504/139 |
| 2010/0056374 | A1 * | 3/2010 | Brewster et al. | 504/136 |
| 2012/0009274 | A1 * | 1/2012 | Young et al. | 424/604 |
| 2012/0094834 | A1 * | 4/2012 | Frank et al. | 504/117 |

FOREIGN PATENT DOCUMENTS

| JP | 2007-1897 | * | 1/2007 |
| WO | 03/047340 | | 6/2003 |
| WO | 2006/097322 | | 9/2006 |
| WO | 2009/141367 A2 | | 11/2009 |

OTHER PUBLICATIONS

International Search Report of PCT/EP2010/003065 mailed May 19, 2011.
International Search Report of EP 12 17 3625 mailed Oct. 24, 2012.

* cited by examiner

*Primary Examiner* — Neil Levy
(74) *Attorney, Agent, or Firm* — Baker Donelson Bearman Caldwell & Berkowitz, PC

(57) ABSTRACT

A description is given of herbicidal compositions comprising
A) tembotrione and
B) at least one additional herbicide.
These compositions exhibit a superior action in comparison with the herbicides applied separately.

17 Claims, No Drawings

SYNERGISTIC HERBICIDAL COMBINATIONS COMPRISING TEMBOTRIONE

CROSS REFERENCE TO RELATED APPLICATIONS

This application claims priority to Priority EP 09007061.6 filed May 27, 2009, the content of which is incorporated herein by reference in its entirety.

BACKGROUND

1. Field of the Invention

The invention relates to the technical field of plant protection compositions which can be used against undesirable plant growth and which comprise, as active substances, a combination of at least two herbicides.

More specifically, it relates to herbicidal combinations for use in rice, corn, and sugarcane which comprise the active substance tembotrione in combination with at least one additional herbicide.

2. Description of Related Art

WO 03/047340 and WO 2007/006415 describe herbicidal compositions comprising tembotrione. However, in practice, there are frequently disadvantages associated with the use of the herbicidal compositions known from these documents. Thus, the herbicidal activity is not always satisfactory or undesirable damage to the rice plants is observed with a satisfactory herbicidal activity.

SUMMARY

It is an object of the present invention to make available additional herbicidal combinations.

A subject matter of the invention is herbicidal combinations, which comprise an effective content of
A) tembotrione and the salts thereof which are standard in agriculture [component (A)]
and
B) at least one compound [component (B)] from the group consisting of the herbicides amicarbazone, aminopyralid, aminocyclopyrachlor, aminocyclopyrachlor-methyl, aminocyclopyrachlor-potassium, cyclosulfamuron, flucetosulfuron, indaziflam, ipfencarbazone, metamifop, orthosulfamuron, penoxsulam, pinoxaden, propyrisulfuron, pyraclonil, pyrasulfotole, pyrimisulfan, pyroxasulfone, pyroxsulam, saflufenacil, 3-chloro-N-[(4,6-dimethoxypyrimidin-2-yl)carbamoyl]-1-methyl-4-(5-methyl-5,6-dihydro-1,4,2-dioxazin-3-yl)-1H-pyrazole-5-sulfonamide, 3-({[5-(difluoromethyl)-1-methyl-3-(trifluoromethyl)-1H-pyrazol-4-yl]methyl}sulfonyl)-5,5-dimethyl-4,5-dihydro-1,2-oxazole, 3-[(2,5-dichloro-4-ethoxybenzyl)sulfonyl]-5,5-dimethyl-1,2-oxazolidine, N-[(4,6-dimethoxypyrimidin-2-yl)carbamoyl]-6-ethyl-2-methylimidazo[1,2-b]pyridazine-3-sulfonamide, 3-({2-[(2-methoxyethoxy)methyl]-6-(trifluoromethyl)pyridin-3-yl}carbonyl)bicyclo[3.2.1]octane-2,4-dione (bicyclopyrone), 2-({2-[(2-methoxyethoxy)methyl]-6-(trifluoromethyl)pyridin-3-yl}carbonyl)cyclohexane-1,3-dione, and methyl 4-amino-3-chloro-6-(4-chloro-2-fluoro-3-methoxyphenyl)pyridine-2-carboxylate.

DETAILED DESCRIPTION OF A PREFERRED EMBODIMENT

In the following, the terms "component (A)" and "herbicide (A)" are to be understood as synonymous. The same applies for the term "component (B)".

The herbicide tembotrione is known, for example, from EP 1 117 639 B1 and from the website "http://www.alanwood.net/pesticides/index.html". The chemical structures of the herbicides mentioned above with their IUPAC names are known, for example, from Ag Chem New Compound Review, Volume 25, 2007, and are mentioned in the following compilation:

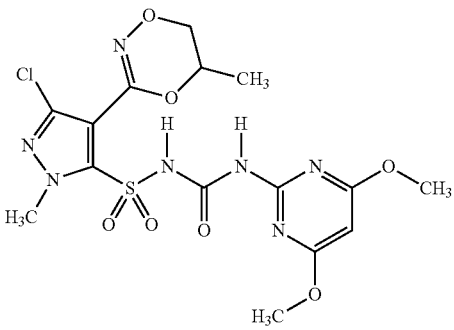

3-chloro-N-[(4,6-dimethoxypyrimidin-2-yl)carbamoyl]-1-methyl-4-(5-methyl-5,6-dihydro-1,4,2-dioxazin-3-yl)-1H-pyrazole-5-sulfonamide

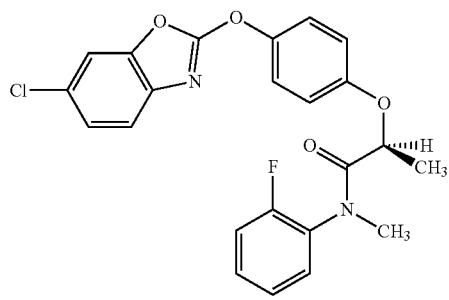

(2S)-2-{4-[(6-chloro-1,3-benzoxazol-2-yl)oxy]phenoxy}-N-(2-fluorophenyl)-N-methylpropanamide

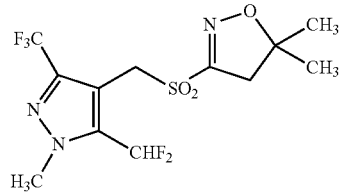

3-({[5-(difluoromethyl)-1-methyl-3-(trifluoromethyl)-1H-pyrazol-4-yl]methyl}sulfonyl)-5,5-dimethyl-4,5-dihydro-1,2-oxazole

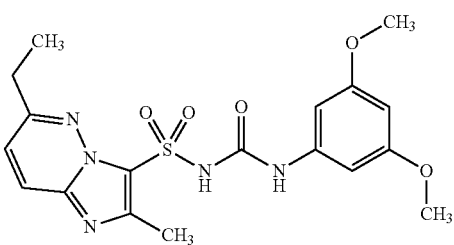

N-[(4,6-dimethoxypyrimidin-2-yl)carbamoyl]-6-ethyl-2-methylimidazo[1,2-b]pyridazine-3-sulfonamide

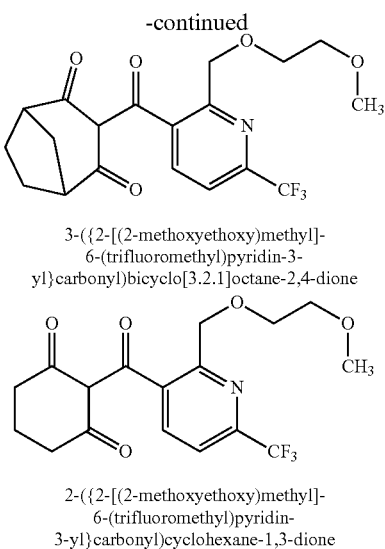

3-({2-[(2-methoxyethoxy)methyl]-
6-(trifluoromethyl)pyridin-3-
yl}carbonyl)bicyclo[3.2.1]octane-2,4-dione 2-({2-[(2-methoxyethoxy)methyl]-
6-(trifluoromethyl)pyridin-
3-yl}carbonyl)cyclohexane-1,3-dione The chemical structures of the other active substances mentioned above with their common names are known, for example, from "The Pesticide Manual", 14th edition, 2006, British Crop Protection Council, and from the website "http://www.alanwood.net/pesticides/index.html". If, in the context of this description, the shortened form of the common name of an active substance is used, this each time includes all common derivatives, such as the esters and salts, and isomers, in particular optical isomers, in particular the commercially available form or forms. If an ester or salt is described by the common name, this also each time includes all other common derivatives, such as other esters and salts, the free acids and neutral compounds, and isomers, in particular optical isomers, in particular the commercially available form or forms. The chemical compound names given describe at least one of the compounds included under the common name, frequently a preferred compound.

The herbicidal combinations according to the invention exhibit, in a preferred embodiment, synergistic effects with, at the same time, high compatibility with regard to cultivated plants, such as cereals, soya, sugarcane, corn and rice, in particular sugarcane, corn and rice. The synergistic effects and the high compatibility with regard to cultivated plants can be observed, e.g., with combined application of the components (A) and (B); however, it can also frequently be detected when the active substances are applied at different times (splitting). It is also possible to apply the individual herbicides in several portions (sequential application), e.g. pre-emergence applications, followed by post-emergence applications or early post-emergence applications, followed by medium or late post-emergence applications.

Preference is given in this connection to the combined or virtually simultaneous application of the active substances of the herbicide combination according to the invention.

The synergistic effects allow a reduction in the application rates of the individual active substances, a greater potency at the same application rate, the control of species hitherto not included (gaps), an extension of the period of application and/or a reduction in the number of individual applications necessary and, as a result for the user, weed combating systems which are more advantageous economically and ecologically.

The invention also includes those herbicidal combinations which, in addition to the components (A) and (B), also comprise one or more additional agrochemical active substances with a different structure, such as herbicides, insecticides, fungicides or safeners. The preferred conditions explained above and below are likewise valid for such herbicidal combinations.

The invention likewise also includes those herbicidal combinations which, in addition to the components (A) and (B), also comprise fertilizers, such as ammonium sulfate, ammonium nitrate, urea, potassium nitrate and mixtures thereof. The preferred conditions explained above and below are likewise valid for such herbicidal combinations.

The invention furthermore also includes those herbicidal combinations which, in addition to the components (A) and (B), also comprise adjuvants, such as emulsifiers, dispersants, mineral and vegetable oils, and mixtures thereof. The preferred conditions explained above and below are likewise valid for such herbicidal combinations.

Herbicidal combinations with a content of one or more of the following combinations of two compounds (A+B) are of particular interest:

tembotrione+amicarbazone, tennbotrione+aminopyralid, tembotrione+aminocyclopyrachlor, tembotrione+aminocyclopyrachlor-methyl, tembotrione+aminocyclopyrachlor-potassium, tembotrione+cyclosulfamuron, tembotrione+indaziflam, tembotrione+flucetosulfuron, tembotrione+ipfencarbazone, tembotrione+metamifop, tembotrione+orthosulfamuron, tembotrione+penoxsulam, tembotrione+pinoxaden, tembotrione+propyrisulfuron, tembotrione+pyraclonil, tembotrione+pyrasulfotole, tembotrione+pyrimisulfan, tembotrione+pyroxasulfone, tembotrione+pyroxsulam, tembotrione+saflufenacil, tembotrione+3-chloro-N-[(4,6-dimethoxypyrimidin-2-yl)carbamoyl]-1-methyl-4-(5-methyl-5,6-dihydro-1,4,2-dioxazin-3-yl)-1H-pyrazole-5-sulfonamide, tembotrione+(2S)-2-{4-[(6-chloro-1,3-benzoxazol-2-yl)oxy]phenoxy}-N-(2-fluorophenyl)-N-methylpropanamide, tembotrione+3-({[5-(difluoromethyl)-1-methyl-3-(trifluoro ethyl)-H-pyrazol-4-yl]methyl}sulfonyl)-5,5-dimethyl-4,5-dihydro-1,2-oxazole, tembotrione+3-[(2,5-dichloro-4-ethoxybenzyl)sulfonyl]-5, 5-dimethyl-1,2-oxazolidine, tembotrione+N-[(4,6-dimethoxypyrimidin-2-yl)carbamoyl]-6-ethyl-2-methylimidazo[1,2-b]pyridazine-3-sulfonamide, tembotrione+3-({2-[(2-methoxyethoxy)methyl]-6-(trifluoromethyl)pyridin-3-yl}carbonyl)bicyclo[3.2.1]octane-2,4-dione, tembotrione+2-({2-[(2-methoxyethoxy)methyl]-6-(trifluoromethyl) pyridin-3-yl}carbonyl)cyclohexane-1,3-dione.

In the herbicidal combinations according to the invention, it is generally necessary to have application rates in the range from 1 to 2000 g, preferably from 10 to 500 g, of active substance per hectare (ai/ha) of the component (A) and from 1 to 2000 g, preferably from 1 to 500 g, of the component (B).

The weight ratios of the component (A) to be used to the component (B) to be used can be varied within a wide range from 1:2000 to 2000:1. Preferably, the weight ratio is in the range from 1:50 to 500:1, in particular in the range from 1:20 to 50:1. Optimum weight ratios can depend on the respective field of application, on the weed spectrum and on the active substance combination used and can be determined in preliminary experiments.

The herbicidal combinations according to the invention are excellently suited to the selective combating of harmful plants in crops, such as cereals, soya, sugarcane, corn and rice, in particular sugarcane, corn and rice.

The herbicidal combinations according to the invention can be used in all types of application normal for rice herbicides. They are particularly advantageously used in the spray application and in the submerged application. In the submerged application, the paddy water already covers the ground by up to 30 mm at the time of the application. The herbicidal combinations according to the invention are then directly placed in the paddy water, e.g. in the form of granules. Worldwide, the spray application is used predominantly with seeded rice and the submerged application is used predominantly with transplanted rice.

The herbicidal combinations according to the invention include a broad weed spectrum. They are suitable for example for the combating of annual and perennial harmful plants, such as, for example, from the genera *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum, Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola* and *Xanthium*.

Because of their herbicidal properties, the herbicidal combinations can also be used for combating harmful plants in crops of genetically modified plants or plants modified by conventional mutagenesis. The transgenic plants are generally distinguished by particular advantageous properties, for example by resistance to certain pesticides, mainly certain herbicides, resistance to plant diseases or causative agents of plant diseases, such as certain insects or microorganisms, such as fungi, bacteria or viruses. Other particular properties relate, e.g., to the harvested crops with regard to amount, quality, storability, composition and special ingredients. Thus, transgenic plants with increased starch content or modified quality of the starch or those with a different fatty acid composition of the harvested crops are known.

Preference is given, with regard to transgenic crops, to the use of the herbicidal combinations according to the invention in economically important transgenic crops of useful and ornamental plants, e.g. of cereals, such as wheat, barley, rye, oats, millet, rice and corn, or also crops of sugar beet, cotton, soya, rape, potato, tomato, peas and other kinds of vegetable.

Preferably, the herbicidal combinations according to the invention can be used as herbicides in crops of useful plants which are resistant to the phytotoxic effects of the herbicides or which have been made resistant by genetic engineering, in particular that of rice.

The herbicidal combinations according to the invention are also distinguished in that the effective dosages of the components (A) and (B) used in the combinations are reduced with regard to an individual dosage, so that a reduction in the necessary application rates of the active substances is rendered possible.

Another subject matter of the invention is a process for combating undesirable plant growth, which comprises the application of one or more herbicides (A) with one or more herbicides (B) to the harmful plants, plant parts thereof or the area under cultivation.

Superadditive (=synergistic) effects occur when herbicides of the type (A) and type (B) are used jointly. The action in the combinations is in this connection stronger than the sum to be expected of the actions of the individual herbicides (A) and (B). The synergistic effects allow a reduction in the application rate, the combating of a broader spectrum of weeds, including grass weeds, a faster onset of the herbicidal action, a longer-lasting action, better control of the harmful plants, with only one or a few applications, and a broadening of the possible application period. These properties are demanded in the practical combating of weeds in order to keep agricultural crops free from undesirable competing plants and accordingly to safeguard and/or to increase the yields in terms of quality and quantity. The technical standard is, with regard to the properties described, clearly exceeded by these new combinations.

The herbicidal combinations according to the invention can exist both as mixed formulations of the components (A) and (B), if appropriate with additional conventional formulation auxiliaries, which are then used in the conventional way diluted with water, or be prepared as "tank mixes" by jointly diluting the separately formulated or partially separately formulated components with water.

The components (A) and (B) can be formulated in different ways, depending on which biological and/or chemical/physical parameters are specified. The following are possible, for example, as general formulation possibilities: wettable powders (WP), emulsifiable concentrates (EC), aqueous solutions (SL), emulsions (EW), such as oil-in-water and water-in-oil emulsions, sprayable solutions or emulsions, oil- or water-based dispersions, suspoemulsions, dustable powders (DP), seed dressings, granules for soil application or broadcasting, water-dispersible granules (WG), ULV formulations, microcapsules or waxes.

The individual formulation types are known in principle and are described, for example, in: Winnacker-Küchler, "Chemische Technologie" [Chemical Technology], Volume 7, C. Hauser Verlag, Munich, 4th edition, 1986; van Valkenburg, "Pesticide Formulations", Marcel Dekker, N.Y., 1973; K. Martens, "Spray Drying Handbook", 3rd Ed., 1979, G. Goodwin Ltd., London. The formulation auxiliaries necessary, such as inert materials, surfactants, solvents and additional additives, are likewise known and are described, for example, in: Watkins, "Handbook of Insecticide Dust Diluents and Carriers", 2nd Ed., Darland Books, Caldwell, N.J.; H.v. Olphen, "Introduction to Clay Colloid Chemistry", 2nd Ed., J. Wiley & Sons, N.Y.; Marsden, "Solvents Guide", 2nd Ed., Interscience, N.Y., 1950; McCutcheon's, "Detergents and Emulsifiers Annual", MC Publ. Corp., Ridgewood, N.J.; Sisley and Wood, "Encyclopedia of Surface Active Agents", Chem. Publ. Co. Inc., N.Y., 1964; Schönfeldt, "Grenzflächenaktive Äthylenoxidaddukte" [Surface-active Ethylene Oxide Adducts], Wiss. Verlagsgesellschaft, Stuttgart, 1976; Winnacker-Küchler, "Chemische Technologie" [Chemical Technology], Volume 7, C. Hauser Verlag Munich, 4th Ed., 1986.

Based on these formulations, combinations with additional pesticidally active substances, such as other herbicides, fungicides or insecticides, and also safeners, fertilizers and/or growth regulators, can also be prepared, e.g. in the form of a ready mix or as tank mix.

Wettable powders are preparations which can be uniformly dispersed in water and which, in addition to the active substance, also comprise ionic or nonionic surfactants (wetting agents, dispersants), e.g. polyoxyethylated alkylphenols, polyethoxylated fatty alcohols or fatty amines, alkanesulfonates or alkylbenzenesulfonates, sodium lignosulfonate, sodium 2,2'-dinaphthylmethane-6,6'-disulfonate, sodium dibutylnaphthalenesulfonate or sodium oleoylmethyltaurinate, in addition to a diluent or inert substance.

Emulsifiable concentrates are prepared by dissolving the active substance in an organic solvent, e.g. butanol, cyclohexanone, dimethylformamide, xylene or also higher-boiling aromatic compounds or hydrocarbons, with addition of one or more ionic or nonionic surfactants (emulsifiers). Use may be made, as emulsifiers, for example, of: calcium alkylarylsulfonates, such as calcium dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dustable powders are obtained by milling the active substance with finely divided solid materials, e.g. talc, natural clays, such as kaolin, bentonite and pyrophyllite, or diatomaceous earth.

Granules can be prepared either by spraying the active substance onto adsorptive granulated inert material or by applying active substance concentrates to the surface of carriers, such as sand or kaolinite, or of granulated inert material using binders, e.g. polyvinyl alcohol, sodium polyacrylate or else mineral oils. Suitable active substances can also be granulated in the standard way for the preparation of fertilizer granules, if desired as a mixture with fertilizers. Water-dispersible granules are generally prepared according to methods such as spray drying, fluidized-bed granulation, disk granulation, mixing with high-speed mixers and extrusion without solid inert material.

The agrochemical compositions generally comprise from 0.1 to 99 percent by weight, in particular from 0.2 to 95 percent by weight, of the components (A) and (B), the following concentrations being normal according to the type of formulation: in wettable powders, the active substance concentration is, e.g., from approximately 10 to 95 percent by weight, the balance for 100 percent by weight consisting of standard formulation constituents. With emulsifiable concentrates, the active substance concentration can be, e.g., from 5 to 80 percent by weight. Formulations in the form of dust for the most part comprise from 5 to 20 percent by weight of active substance, sprayable solutions from approximately 0.2 to 25 percent of active substance. With granules, such as dispersible granules, the active substance content partly depends on whether the active compound is present in liquid or solid form and on which granulation auxiliaries and fillers are being used. With water-dispersible granules, the content is generally between 10 and 90 percent by weight. In addition, the active substance formulations mentioned comprise, if appropriate, the stickers, wetting agents, dispersing agents, emulsifying agents, preservatives, antifreeze agents, solvents, fillers, colorants, carriers, antifoaming agents, evaporation inhibitors, pH regulators or viscosity regulators which are standard in each case.

For use, the formulations existing in commercially available form are, if appropriate, diluted in the standard way, e.g. using water for wettable powders, emulsifiable concentrates, dispersions and water-dispersible granules. Compositions in the form of dusts, soil granules, granules for broadcasting and sprayable solutions are normally not diluted further with additional inert materials before use.

The herbicidal combinations can be applied to the plants, plant parts, plant seeds or the area under cultivation (arable land), preferably to the green plants and plant parts and, if appropriate, additionally to the arable land.

One possibility of use is the joint application of the herbicidal combinations in the form of tank mixes, where the concentrated formulations, which are optimally formulated, of the components are mixed together in the tank with water and the spray mixture obtained is applied.

A joint herbicidal formulation of the herbicidal combinations according to the invention of components (A) and (B) has the advantage of being able to be applied more easily because the amounts of the components have already been adjusted to the correct ratio to one another. Moreover, the auxiliaries in the formulation can be optimally matched to one another, while a tank mix of different formulations can give undesirable combinations of auxiliaries.

A. FORMULATION EXAMPLES a) A dustable powder is obtained by mixing 10 parts by weight of component (A) or (B) or a mixture thereof and 90 parts by weight of talc as inert material and comminuting in a hammer mill.

b) A wettable powder readily dispersible in water is obtained by mixing 25 parts by weight of component (A) or (B) or a mixture thereof, 64 parts by weight of kaolin-comprising quartz as inert material, 10 parts by weight of potassium lignosulfonate and 1 part by weight of sodium oleoylmethyltaurinate as wetting and dispersing agent and milling in a pin mill.

c) A dispersion concentrate readily dispersible in water is obtained by mixing 20 parts by weight of component (A) or (B) or a mixture thereof with 6 parts by weight of alkylphenol polyglycol ether (Triton X 207), 3 parts by weight of isotridecanol polyglycol ether (8 EO) and 71 parts by weight of paraffinic mineral oil (boiling range, e.g., approximately 255 to 277° C.) and milling in a friction ball mill to a fineness of less than 5 microns.

d) An emulsifiable concentrate is obtained from 15 parts by weight of component (A) or (B) or a mixture thereof, 75 parts by weight of cyclohexanone as solvent and 10 parts by weight of oxyethylated nonylphenol as emulsifier.

e) A water-dispersible granule is obtained by mixing
75 parts by weight of component (A) or (B) or a mixture thereof,
10 parts by weight of calcium lignosulfonate,
5 parts by weight of sodium lauryl sulfate,
3 parts by weight of polyvinyl alcohol and
7 parts by weight of kaolin
milling on a pin mill and granulating the powder in a fluidized bed by spraying on water as granulation liquid.

f) A water-dispersible granule is also obtained by homogenizing and precomminuting
25 parts by weight of component (A) or (B) or a mixture thereof,
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water
on a colloid mill, subsequently milling on a bead mill and atomizing and drying the suspension thus obtained in a spray tower using a single-substance nozzle.

B. BIOLOGICAL EXAMPLES

1. Pre-Emergence Weed Action

Seeds or root pieces of mono- and dicotyledonous weed plants are placed in sandy clay soil in pots and covered with earth. In the case of spray application, the compositions formulated in the form of concentrated aqueous solutions, wettable powders or emulsion concentrates are then applied in different dosages to the surface of the covering earth as aqueous solution, suspension or emulsion with a water application rate of 600 to 800 l/ha (corrected). Immediately up to a few days after application, the test receptacles accumulate water over the ground surface by up to 30 mm. In the case of the water application (submerged application), on the other hand, the ground in the closed test receptacle is already covered with the paddy water up to 30 mm at the time of the application. The formulated active substances are here, for example in the form of granules, added directly to the paddy water. After the treatment, the pots are placed in the greenhouse and kept under good growing conditions for the weeds. The plant damage or emergence damage after the emergence of the test plants after a test period of 3 to 4 weeks is evaluated visually in comparison with untreated controls. As the test results show, the compositions according to the invention exhibit a very good herbicidal pre-emergence activity against a broad spectrum of weeds, including grass weeds. In this connection, actions of the combinations according to the invention which exceed the formal sum of the actions of the herbicides when applied individually are frequently observed. The values observed for the tests show, with suitable low dosages, an action of the combinations which lies above the expected values according to Colby.

Evaluation and Appraisal of the Synergistic Herbicidal Actions:

The herbicidal activity of the active substances or active substance mixtures was evaluated visually from the treated variants in comparison with untreated control variants. In this connection, damage to and development of all plant parts above ground was included. The evaluation was carried out according to a percentage scale (100% action=all plants dead; 50% action=50% of the plants and green plant parts dead; 0% action=no recognizable action=as untreated control plot).

2. Post-Emergence Weed Action

Seeds or root pieces of mono- and dicotyledonous weeds are placed in sandy clay soil in pots, covered with earth and secured in a greenhouse under good growing conditions (temperature, air humidity, water supply). Approximately three weeks after sowing, the test plants are treated with the compositions according to the invention. The compositions according to the invention formulated as wettable powders or as emulsion concentrates are sprayed, in spray application, on to the green plant parts in different dosages with a water application rate of 600 to 800 l/ha (corrected). Immediately up to a few days after application, the test receptacles accumulate water over the ground surface by up to 30 mm. With the water application (submerged application), on the other hand, the ground in the closed test receptacle is already covered with the paddy water up to 30 mm at the time of the application. The formulated active substances are here added directly to the paddy water. After an exposure time of the test plants in the greenhouse of an additional 3 to 4 weeks under optimum growing conditions, the effect of the preparations is evaluated visually in comparison with untreated controls. The compositions according to the invention exhibit, even in post-emergence, a very good herbicidal activity against a broad spectrum of economically important weeds, including grass weeds. In this connection, actions of the combinations according to the invention which exceed the formal sum of the actions of the herbicides when applied individually are frequently observed. The values observed for the tests show, with suitable low dosages, an action of the combinations which lies above the expected values according to Colby.

3. Herbicidal Action and Cultivated Plant Compatibility (Field Trials)

Cultivated plants were grown in the field on plots under natural field conditions, seeds or root pieces of typical harmful plants having been sown or planted or natural weed infestation having been used. The treatment with the compositions according to the invention was carried out as spray application or as water application (submerged application) after the emergence of the harmful plants and the cultivated plants, generally in the 2- to 4-leaf stage; in some cases (as indicated), the application of individual active substances or active substance combinations was carried out before emergence or, as sequential treatment, is some cases before emergence and/or after emergence. After use, e.g. 2, 4, 6 and 8 weeks after application, the action of the preparations was evaluated visually in comparison with untreated controls (cf. evaluation in example 1). The compositions according to the invention also exhibit, in the field trial, a synergistic herbicidal activity against the broad spectrum of economically important weeds, including grass weeds. The comparison showed that the combinations according to the invention for the most part exhibit a greater, in some cases a much greater, herbicidal action than the sum of the actions of the individual herbicides and accordingly points to a synergy. In addition, in substantial sections of the evaluation period, the actions lay above the expected values according to Colby and accordingly likewise point to a synergy. In comparison, the cultivated plants were undamaged or only slightly damaged as a result of the treatments with the herbicidal compositions.

When the combinations according to the invention are used, herbicidal actions on a harmful plant species which exceed the formal sum of the actions of the herbicides present when applied singly are frequently observed. Alternatively, it can in many cases be observed that a lower application rate for the herbicidal combination is needed in order to achieve, in comparison with the individual preparations, the same action with a harmful plant species. Such improvements in action or improvements in effectiveness or economies in application rate are a strong indication of a synergistic effect.

If the observed activity values already exceed the formal sum of the values for the tests with individual applications, then they likewise exceed the expected value according to Colby, which is calculated according to the following formula and is likewise regarded as an indication of synergy (cf. S. R. Colby in Weeds, 15 (1967), pp. 20 to 22):

$$E = A + B - \frac{A \times B}{100}$$

In this connection:
A, B=action of the component A or B in percent at a dosage of a or b grams ai/ha.
E=expected value in % at a dosage of a+b grams ai/ha.

The values observed for the test examples mentioned above are greater than the expected values according to Colby.

The abbreviation IPOHE is the harmful plant *Ipomoea hederacea*.

In addition to tembotrione, the following herbicides were used in the exemplary embodiments:

B1: amicarbazone, B2: aminopyralid, B4: aminocyclopyrachlor, B6: cyclosulfamuron, B7: indaziflam, B8: flucetosulfuron, B9: ipfencarbazone, B10: metamifop, B11: orthosulfamuron, B12: penoxsulam, B13: pinoxaden, B14: propyrisulfuron, B15: pyraclonil, B16: pyrasulfotole, B17: pyrimisulfan, B18: pyroxasulfone, B19: pyroxsulam, B20: saflufenacil, B21: 3-chloro-N-[(4,6-dimethoxypyrimidin-2-yl)carbamoyl]-1-methyl-4-(5-methyl-5,6-dihydro-1,4,2-dioxazin-3-yl)-1H-pyrazole-5-sulfonamide.

| Post-emergence action | | | |
|---|---|---|---|
| Compound | Dosage [g/ha] | Action against IPOHE | Expected value according to Colby |
| tembotrione | 50 | 40% | |
| B1 | 125 | 20% | |
| tembotrione + B1 | 50 + 125 | 75% | 52% |
| B2 | 75 | 30% | |
| tembotrione + B2 | 50 + 75 | 85% | 58% |
| B4 | 50 | 35% | |
| tembotrione + B4 | 50 + 50 | 93% | 61% |
| B6 | 50 | 20% | |
| tembotrione + B6 | 50 + 50 | 65% | 52% |
| B7 | 25 | 25% | |
| tembotrione + B7 | 50 + 25 | 70% | 55% |
| B8 | 50 | 20% | |
| tembotrione + B8 | 50 + 50 | 77% | 52% |
| B9 | 50 | 25% | |
| tembotrione + B9 | 50 + 50 | 67% | 55% |
| B10 | 75 | 15% | |
| tembotrione + B10 | 50 + 75 | 65% | 49% |
| B11 | 30 | 40% | |
| tembotrione + B11 | 50 + 30 | 90% | 64% |
| B12 | 15 | 20% | |
| tembotrione + B12 | 50 + 15 | 75% | 52% |
| B13 | 30 | 15% | |
| tembotrione + B13 | 50 + 30 | 60% | 49% |
| B14 | 50 | 30% | |
| tembotrione + B14 | 50 + 50 | 80% | 58% |
| B15 | 75 | 30% | |
| tembotrione + B15 | 50 + 75 | 85% | 58% |
| B16 | 25 | 50% | |
| tembotrione + B16 | 50 + 25 | 95% | 70% |
| B17 | 50 | 20% | |
| tembotrione + B17 | 50 + 50 | 85% | 52% |
| B18 | 75 | 15% | |
| tembotrione + B18 | 50 + 75 | 85% | 49% |
| B19 | 15 | 20% | |
| tembotrione + B19 | 50 + 15 | 75% | 52% |
| B20 | 10 | 45% | |
| tembotrione + B20 | 50 + 10 | 95% | 67% |
| B21 | 50 | 15% | |
| tembotrione + B21 | 50 + 50 | 75% | 49% |

The invention claimed is:

1. A synergistic herbicidal combination, which comprises an effective amount of
   Component A) tembotrione and/or a salt thereof which is standard in agriculture
   and
   Component B) at least one compound selected from the group consisting of the herbicides amicarbazone, aminopyralid, aminocyclopyrachlor, cyclosulfamuron, flucetosulfuron, indaziflam, ipfencarbazone, metamifop, orthosulfamuron, penoxsulam, pinoxaden, propyrisulfuron, pyraclonil, pyrasulfotole, pyrimisulfan, pyroxsulam, saflufenacil, and
   3-chloro-N-[(4,6-dimethoxypyrimidin-2-yl)carbamoyl]-1-methyl-4-(5-methyl-5,6-dihydro-1,4,2-dioxazin-3-yl)-1H-pyrazole-5-sulfonamide,
   wherein the weight ratio A:B of the combined herbicides (A) and (B) lies in a range from 1:20 to 50:1.

2. A synergistic herbicidal combination as claimed in claim 1, which comprises 0.1-99% by weight of herbicides (A) and (B) and from 99 to 0.1% by weight of at least one formulating agent standard in plant protection.

3. A process for combating undesirable plant growth, said process comprising applying a combination as claimed in claim 1, which comprises applying at least one herbicide (A) and at least one herbicide (B) to a harmful plant, a plant part thereof and/or an area under cultivation.

4. A synergistic herbicidal composition for combating undesirable plant growth, said composition comprising a combination of herbicides (A) and (B) as defined in claim 1.

5. A synergistic herbicidal synergistic combination as claimed in claim 1, which comprises as component (B), 3-chloro-N-[(4,6-dimethoxypyrimidin-2-yl)carbamoyl]-1-methyl-4-(5-methyl-5,6-dihydro-1,4,2-dioxazin-3-yl)-1H-pyrazole-5-sulfonamide.

6. A synergistic herbicidal combination as claimed in claim 1, wherein the weight ratio A:B of the combined herbicides (A) and (B) lies in a range from 1:2.5 to 5:1.

7. A synergistic herbicidal synergistic combination as claimed in claim 1, which comprises as component (B), amicarbazone.

8. A synergistic herbicidal synergistic combination as claimed in claim 1, which comprises as component (B), aminopyralid.

9. A synergistic herbicidal synergistic combination as claimed in claim 1, which comprises as component (B), aminocyclopyrachlor.

10. A synergistic herbicidal synergistic combination as claimed in claim 1, which comprises as component (B), flucetosulfuron.

11. A synergistic herbicidal synergistic combination as claimed in claim 1, which comprises as component (B), indaziflam.

12. A synergistic herbicidal synergistic combination as claimed in claim 1, which comprises as component (B), pyrimisulfan.

13. A synergistic herbicidal synergistic combination as claimed in claim 1, which comprises as component (B), pyrasulfotole.

14. A synergistic herbicidal synergistic combination as claimed in claim 1, which comprises as component (B), orthosulfamuron.

15. A synergistic herbicidal synergistic combination as claimed in claim 1, which comprises as component (B), penoxsulam.

16. A synergistic herbicidal synergistic combination as claimed in claim 1, which comprises as component (B), pyroxsulam.

17. A synergistic herbicidal synergistic combination as claimed in claim 1, which comprises as component (B), saflufenacil.

* * * * *